United States Patent [19]

Hopenfeld

[11] Patent Number: 4,779,453
[45] Date of Patent: Oct. 25, 1988

[54] METHOD FOR MONITORING THINNING OF PIPE WALLS

[76] Inventor: Joram Hopenfeld, 1724 Yale Pl., Rockville, Md. 20850

[21] Appl. No.: 122,126

[22] Filed: Nov. 18, 1987

[51] Int. Cl.$^4$ .................. G01N 17/00; G01M 3/22
[52] U.S. Cl. .................................. 73/86; 73/40.7; 250/303
[58] Field of Search ............... 73/86, 40.7; 250/302, 250/303, 260

[56] References Cited

U.S. PATENT DOCUMENTS 3,532,797 10/1970 Lunig .................................. 73/86 X
4,389,877 6/1983 Lacey .................................. 73/86 X

FOREIGN PATENT DOCUMENTS 1086629 5/1986 Japan .................................. 73/40.7
1188595 10/1985 U.S.S.R. ............................. 73/86

Primary Examiner—Stewart J. Levy
Assistant Examiner—Joseph W. Roskos
Attorney, Agent, or Firm—Epstein & Edell

[57] ABSTRACT

A method of monitoring thinning of pipe walls in a piping system including selecting locations to be monitored, normally those pipes particularly susceptible to thinning from erosion/corrosion, boring holes in the outer surfaces of the pipes at the selected locations to depths greater than the thickness at which the pipes will rupture to leave predetermined residual wall thicknesses between the ends of the holes and the inner surfaces of the pipe walls, inserting tracer materials in the holes to be released in the pipes when pipe wall thinning exceeds the residual wall thicknesses of the holes, monitoring fluid flow through the piping system to sense the presence of tracer materials in the fluid, and determining the location of the hole from which a sensed tracer material was released to permit pipe wall thinning to be determined prior to pipe rupture allowing repair or replacement during scheduled downtime of the piping system. Preferably, a series of spaced holes are bored to differing depths at each location such that, knowing the difference in depth and thus residual thickness between holes and the time period between detection of tracer materials from each hole, the rate of pipe wall thinning can be determined, and the period of time in which the pipe can be safely repaired can be calculated.

16 Claims, 3 Drawing Sheets

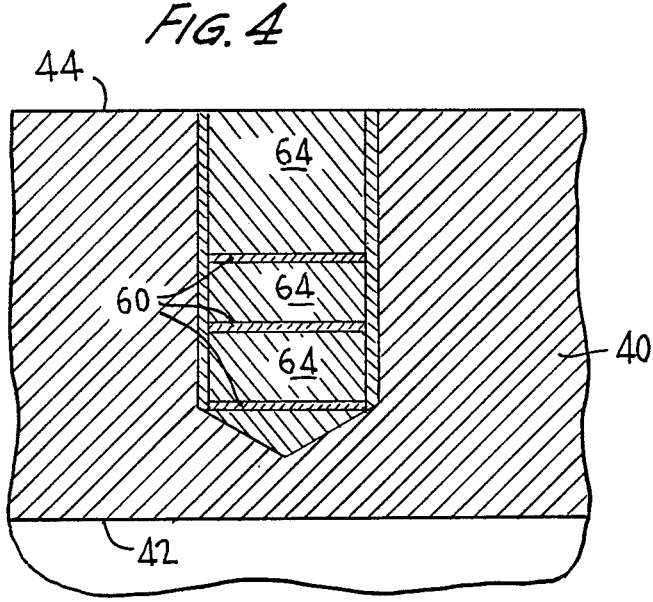
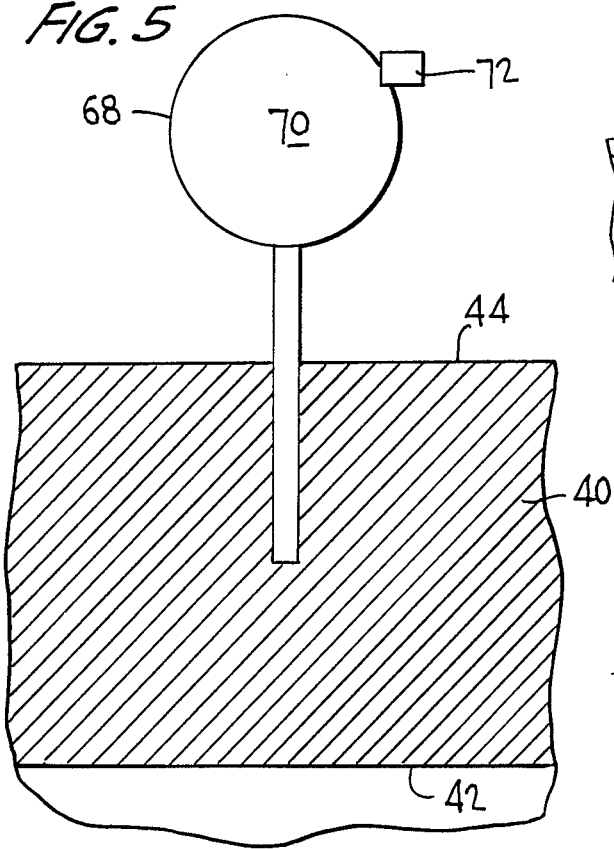
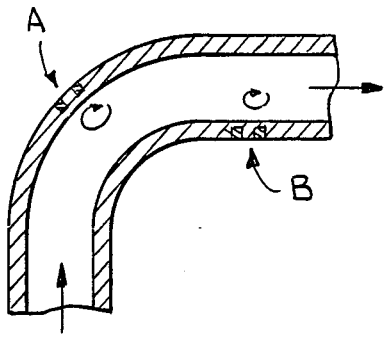
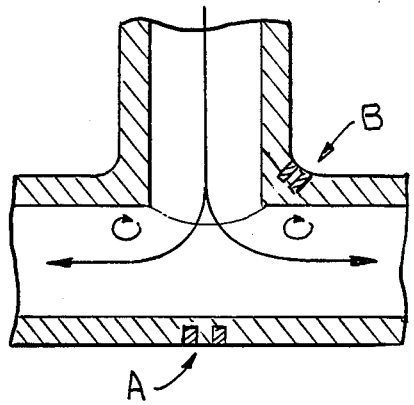
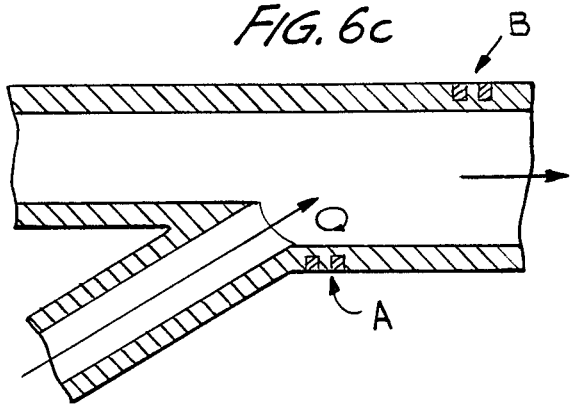
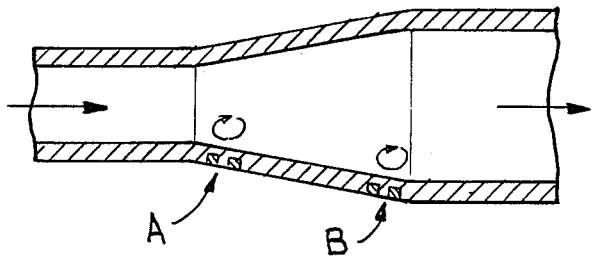

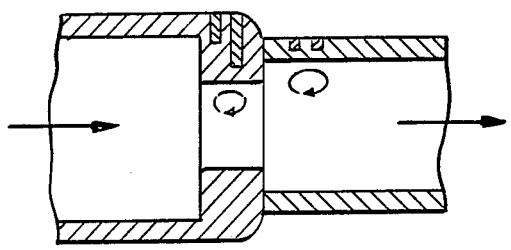
FIG. 6e
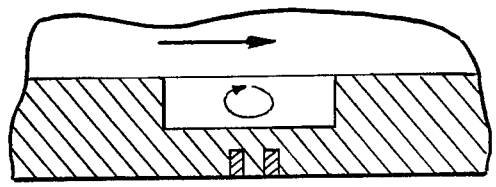
FIG. 6g
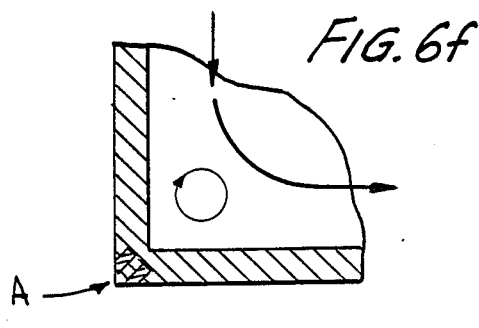
FIG. 6f
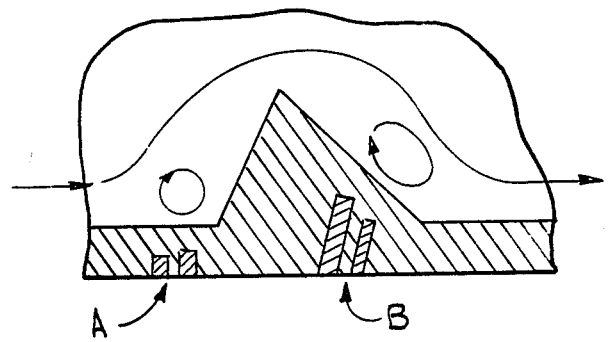
FIG. 6h
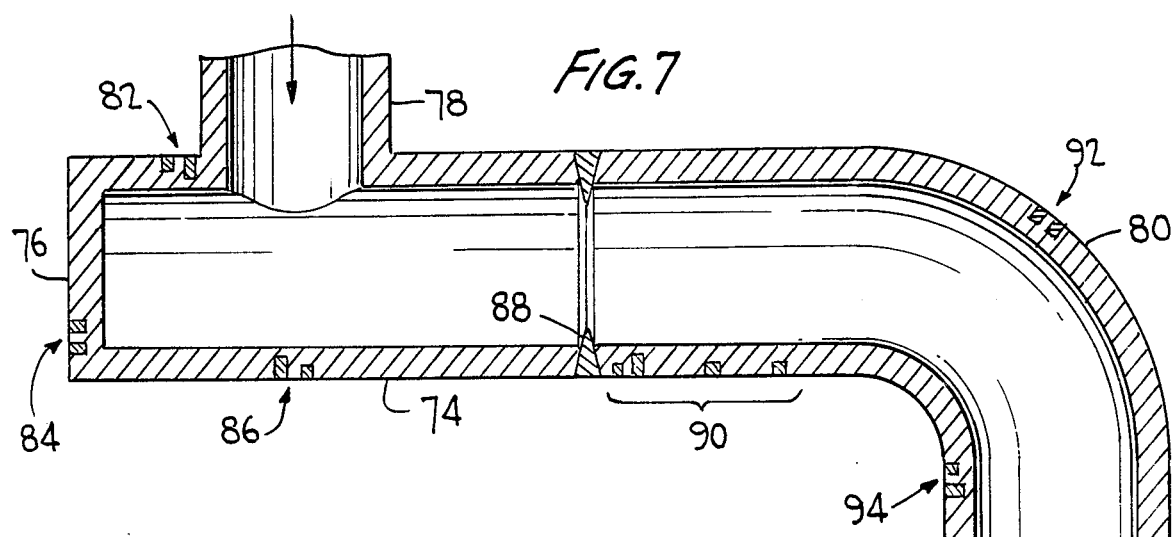
FIG. 7
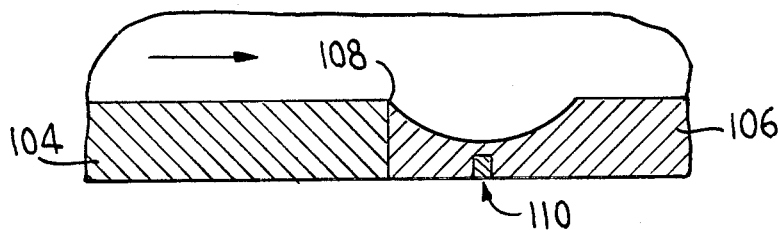
FIG. 8
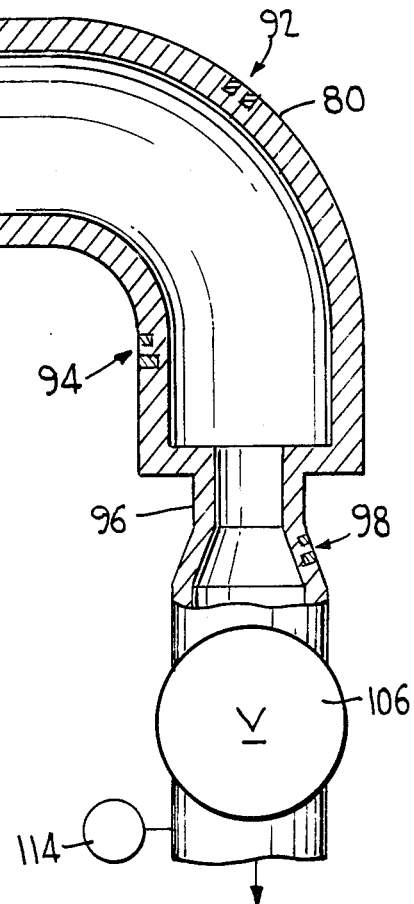

METHOD FOR MONITORING THINNING OF PIPE WALLS

BACKGROUND OF THE INVENTION

Field of the Invention

The present invention pertains to monitoring the thinning of pipes and, more particularly, to a method for monitoring thinning of pipe walls in piping systems to allow repair or replacement of pipes having unduly thinned walls prior to rupture of the pipes.

Discussion of the Prior Art

Many efforts have been made in the past to detect thinning of pipe walls prior to rupture of the pipes; however, such systems have either been ineffective or economically infeasible due to the cost of actually determining wall thickness and/or the downtime required for inspection. Pipe thinning in high pressure piping systems, such as those in the power generating industry, present major safety hazards since rupture or failure of pipes in such systems can cause catastrophic accidents.

Pipe thinning due to erosion/corrosion has become a particular problem in the secondary piping systems on the liquid side of power generating plants since rupture or failure of pipes in such piping systems present great potential for bodily injury and economic injury due to the unscheduled downtime. In one accident in a power generating plant that had been in existence for only one-third of its design life, a pipe elbow ruptured, and measurement of thinning caused by erosion/corrosion revealed that the wall thickness at the time of rupture was 0.01 inches, thinned from a beginning of life thickness of 0.50 inches.

One manner in which to combat the dangerous conditions existing from pipe thinning in the power generating industry is to replace commonly used low carbon steel pipes with pipes made of steel containing more chromium; however, such replacement is economically prohibitive due to the cost of replacement coupled with the downtime of the power generating plant.

In view of the above, it will be appreciated that there is a great need for advanced warning of pipe thinning to permit repair or replacement of unduly thinned pipes during scheduled plant downtime and, or course, prior to rupture. Ultrasonic inspection systems currently employed to detect pipe thinning require a sensor to be placed against the outer wall of pipes to be tested and moved from point to point in areas vulnerable to erosion/corrosion. Such ultrasonic inspection has the disadvantage of requiring periodic access to the piping system necessitating extensive removal of insulation from pipes as well as being expensive from a manpower standpoint and from requiring access into power generator plants. The result is that ultrasonic inspection is limited, economically, to keep costs under control, and many pipes are not entirely inspected but rather are inspected only by selective sampling. Such selective inspection is inherently unreliable as evidenced by a recent accident caused by rupture of a steam generator tube at a power generating plant immediately after the plant was brought to power following periodic inspection, the ruptured tube not being selected for inspection.

Other methods of detecting thinning of walls include drilling wells into a pipe wall from the outer side such that a leak occurs after a predetermined amount of pipe wall thinning, as exemplified by U.S. Pat. No. 1,977,177 to De Florenz and No. 2,083,011 to Ducommun. It has also been known to bore holes entirely through the walls of pipes and insert plugs therein such that wall thickness can be determined by removing the plugs and visually inspecting the walls. Additionally, resistive electrical sensors have been imbedded in walls to provide an electrical indication due to resistance change of wear or erosion of the walls as exemplified by U.S. Pat. No. 3,015,950 to Doctor et al.

The use of tracer materials to indicate wear of mechanical elements is exemplified by U.S. Pat. No. 4,027,157 to Gerve' et al disclosing radioactively marked machine components having "wear fragments" introduced into a lubricant circuit to pass through a measuring chamber surrounding a radiation detector to characterize the components exposed to wear via the detected energy of the gamma quanta for multiple-component measurements; U.S. Pat. No. 2,938,125 to Marak disclosing impregnating the surface of a base material, such as a bearing or a piston, with a radioactive or chemically detectable substance and coating the impregnated surface with a wear resistant material free of the substance such that wear exposes the substance and the substance appears in the lubricant and can be detected, such as with the use of a geiger counter; U.S. Pat. No. 2,658,724 to Arps disclosing capsules of tracer material inserted in teeth of a drill for release into the drill to produce a warning signal indicative of drill wear; U.S. Pat. No. 3,797,896 to Bardach disclosing a bearing lined with radioactive atom dopants of two species for detecting an individual bearing experiencing wear through; and U.S.S.R. Pat. No. 1,004,835 disclosing multiple radio-nuclide marks and loss of activation of the marks to determine the degree of breakdown of the surface of an article. U.S. Pat. No. 2,994,778 to Marsh, No. 3,348,052 to Raifsnider et al and No. 3,678,273 to Lewis are exemplary of the positioning of radioactive, abradable material in a fluid stream to monitor the corrosivity of a fluid.

The detection of fuel pin failures by monitoring cover gas is discussed in an article from the Proceedings of the International Conference on Liquid Metal Technology in Energy Production, May 3-6, 1976, pages 777 through 781 entitled "On Line Radiometric Analysis of FFTF's Cover Gas-Basic Analytical Features" and on pages 494 and 495 of *Fast Breeder Reactors* by Waltar and Reynolds, Pergamon Press, wherein it is indicated that the fuel assembly containing a failed fuel pin can be determined from unique blends of stable xenon and krypton isotopes injected in the fusion gas plenum of each fuel pipe during fabrication thereof.

The prior art, thus, is cognizant of the need to detect pipe thinning and of the use of tracer materials to detect corrosion or wear of machine parts; however, there exists no economically feasible yet dependable and accurate method to detect or monitor pipe thinning without requiring periodic access to the piping system. More particularly, methods for detecting wear of machine parts with the use of tracer materials have the disadvantages of requiring special machine part fabrication and/or machine disassembly for implementation, none of these methods being designed or suitable for detecting or monitoring thinning of pipe walls.

SUMMARY OF THE INVENTION

Accordingly, it is an object of the present invention to overcome the above mentioned disadvantages of the prior art to permit economically feasible, dependable and accurate monitoring of pipe wall thinning in piping systems.

Another object of the present invention is to modify a piping system with minimal downtime to permit continuous monitoring of pipe wall thinning.

An additional object of the present invention is to continuously monitor pipe wall thinning in a piping system requiring access to the piping system only to sense tracer materials. The sensing can be accomplished on-line with instrumentation presently used to sense radioactivity in power generating plants when radioactive tracer materials are used or the sensing can be accomplished by periodic sampling and analysis of the fluid in the piping system.

A further object of the present invention is to monitor pipe wall thinning in a piping system to detect wall thinning beyond predetermined limits and identify which pipe or location in the system has undergone such thinning.

The present invention has another object in that pipe wall thinning in a piping system is monitored to detect wall thinning beyond predetermined limits and to determine the rate of wall thinning at various locations within the piping system and thereby permit advance planning for timely pipe repair or replacement.

Some of the advantages of the present invention over the prior art are that the monitoring method can be implemented in existing piping systems with minimal downtime and expense, once tracer materials are in place in a piping system continuous or periodic analysis of the fluid in the piping system for the tracer materials indicative of pipe thinning can be accomplished at negligible cost, by determining rate of thinning repair or replacement of pipes can be accomplished during normal scheduled downtimes of the piping system, and locations of thinning can be verified by radiation checking or visual inspection.

The present invention is generally characterized in a method of monitoring thinning of pipe walls in a piping system including the steps of boring holes externally in the walls of the pipes at predetermined locations to depths larger than the thicknesses at which the pipes will rupture leaving residual wall thicknesses between the ends of the holes and the internal surfaces of the walls, inserting tracer materials in the holes to be released into fluid in the piping system when pipe wall thinning exceeds the residual wall thickness at any of the holes, monitoring fluid flow through the piping system to sense the presence of the tracer materials in the fluid, and determining the location of the hole from which the tracer material was released whereby pipe wall thinning can be detected prior to rupture and thinning of particular pipes within the piping system can be determined to facilitate repair with minimal downtime of the piping system.

The present invention is further generally characterized in a method of monitoring thinning of a pipe carrying a fluid including the steps of boring a hole in the outer wall of the pipe to a predetermined depth greater than the wall thickness at which the pipe will rupture to produce a blind end spaced from the internal surface of the pipe wall by a predetermined residual wall thickness, inserting a tracer material in the hole adjacent the blind end, and monitoring the fluid passing through the pipe to sense presence of the tracer material whereby pipe thinning corresponding to the residual wall thickness can be detected.

Other objects and advantages of the present invention will become apparent from the following description of the preferred embodiments taken in conjunction with the drawings.

BRIEF DESCRIPTION OF THE DRAWINGS

FIG. 4 is a sectional view of another tracer material insert for use with the present invention.

FIG. 5 is a diagrammatic view of a chemical tracer material insert for use with the present invention.

FIGS. 6a–6h show piping system components subject to thinning from erosion/corrosion with tracer inserts located at preferred positions.

FIG. 7 is a diagrammatic illustration of a portion of a piping system with tracer material inserts in accordance with the method of the present invention.

FIG. 8 is a partial section of the position of a tracer material insert adjacent a junction of pipes made of different materials.

DESCRIPTION OF THE PREFERRED EMBODIMENTS

Figure 1:
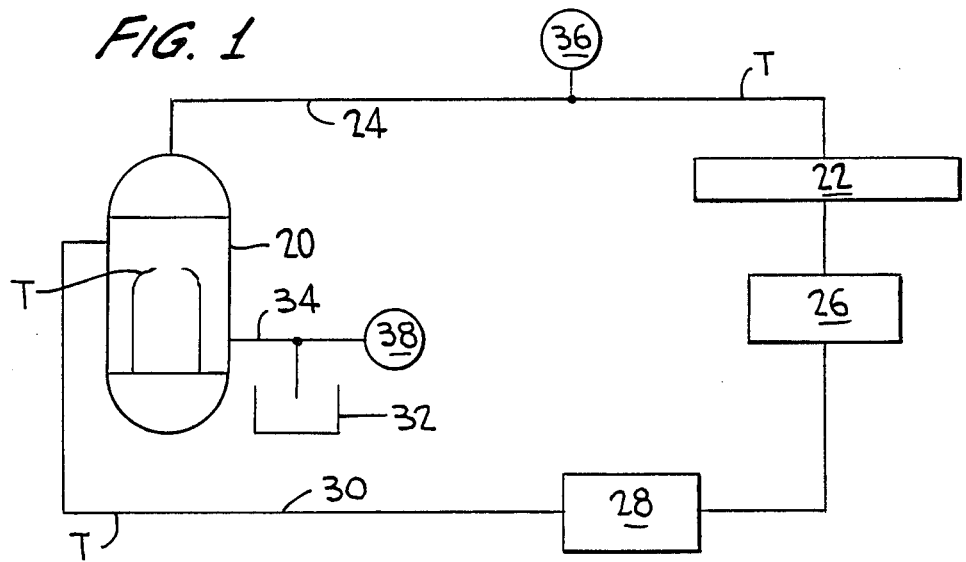
FIG. 1 is a diagrammatic block diagram of a secondary loop piping system in a pressurized light water power generating plant of the type in which the method of present invention can be employed.

The method for monitoring thinning of pipes in accordance with the present invention will be described with reference to a typical secondary loop piping system in a pressurized light water power generating plant, as shown in FIG. 1; however, the present invention can be used to detect thinning of pipes in any piping system. A typical power generating plant will include a number of secondary loops in parallel with a reactor vessel, each loop including a steam generator 20 from which steam is supplied to turbines 22 via a pipe 24. The effluent from the turbines is supplied to a condenser 26 and is pumped back to the steam generator 20 through a series of heaters 28 and a pipe 30. A blowdown tank 32 communicates with the steam generator via a pipe 34. The steam and water sides of the secondary loop are extensively sampled for radiation, such as by on-line radiation detectors 36 and 38 connected with pipes 24 and 34, respectively. Since the secondary loop components are under pressure and are normally radioactively contaminated, it is essential from a safety standpoint to assure that no leaks occur and that no components break. Extensive efforts have been expended toward predicting which components of the loop are primarily subject to erosion/corrosion causing pipe thinning and subsequent breakage if undetected. For example, the Electric Power Research Institute has produced a computer program for ranking of piping components in order of susceptibility to single phase erosion/corrosion. With respect to the secondary loop shown in FIG. 1, typical areas highly susceptible to thinning caused by erosion/corrosion are indicated at T and include the water feed pipe 30, the steam feed pipe 24 and distribution and internal pipes within the steam generator.

Figure 2:
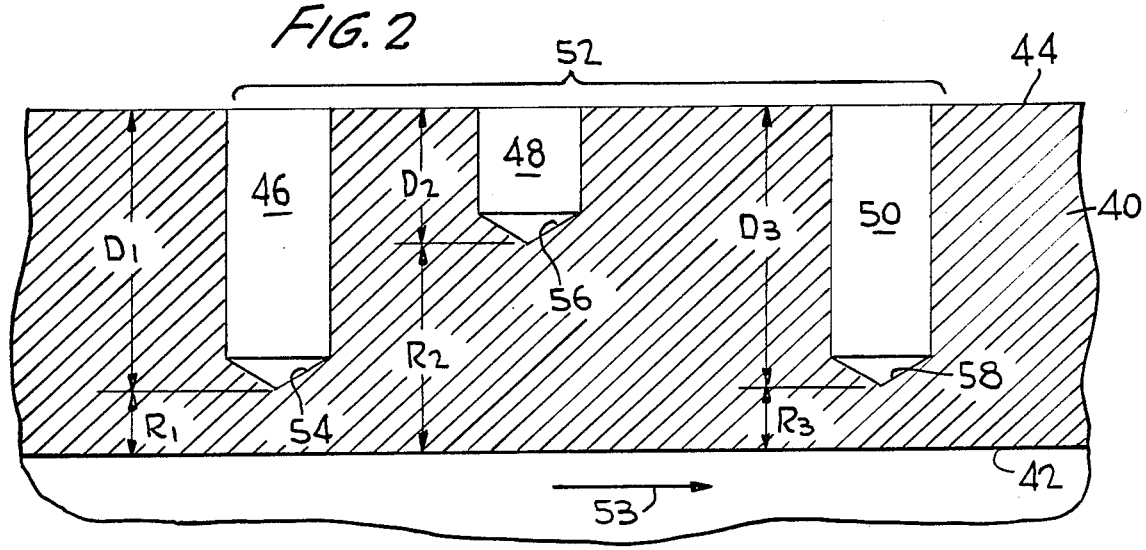
FIG. 2 is a sectional view of a pipe wall having holes for receiving tracer material in accordance with the present invention.

In accordance with the present invention, pipe walls at locations particularly susceptible to thinning, such as those indicated at T, are externally bored to form holes extending radially inwardly from the outer surface of the pipe walls toward the inner surface. With reference to FIG. 2, a pipe to be monitored has a wall 40 with an inner surface 42 subject to erosion/corrosion due to fluid flow therethrough and an outer surface 44 accessible for boring holes 46, 48 and 50 in a location selected for monitoring generally indicated at 52. The holes have a diameter within the preferred range of from 0.125 to 0.250 inch and are spaced from each other along the direction of flow within the pipe shown by arrow 53. A single hole can be used at any location; however, the invention will be described with the use of a plurality of holes to provide more meaningful information relating to rate of thinning. Hole 46 is bored to a depth $D_1$ to have a blind end 54 spaced from inner surface 42 by a distance $R_1$ referred to as residual thickness. Hole 48 is bored to a smaller depth $D_2$ terminating at a blind end 56 defining a larger residual thickness $R_2$ while hole 50 is bored to a depth $D_3$ to terminate at a blind end 58 defining a residual thickness $R_3$ where $D_3$ and $R_3$ are substantially the same as $D_1$ and $R_1$.

The residual thickness $R_1$ is determined to allow sufficient time to elapse before a first indication of thinning is produced thereby providing an accurate and reliable thinning rate to be calculated while depth $D_2$ is representative of a pipe wall thickness larger than the pipe wall thickness required for structural integrity of the pipe, $D_{min}$, the difference between $D_2$ and $D_{min}$ being designated $\Delta D$ which is large enough to allow sufficient time, TR, for planning pipe repair or replacement during scheduled downtimes. If C denotes the expected thinning rate, $\Delta D$ is given by $\Delta D = C \times TR$; and, since TR is piping system specific, the determination of depths of the holes will be calculated for each system. Residual wall thickness $R_1$ is preferably one-half residual wall thickness $R_2$; and, by use of wall thinning indications from holes 46 and 48, two data points are provided allowing the plotting of a curve based on two thinning rates to determine a maximum thinning rate and, therefrom, a minimum time remaining for safe operation prior to pipe rupture.

Figure 3:
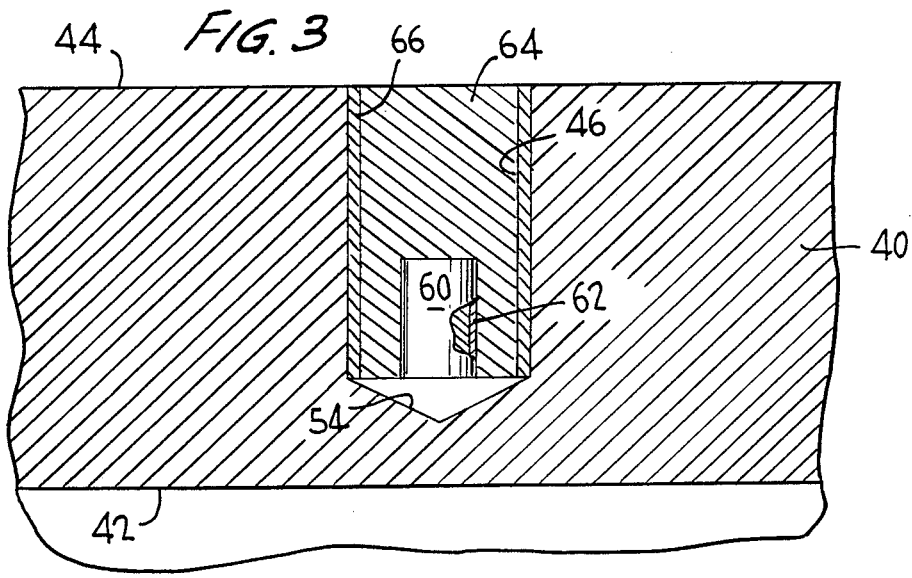
FIG. 3 is a sectional view of a tracker material insert for use with the present invention.

Tracer material is inserted in each hole as described with respect to FIGS. 3, 4 and 5. As shown in FIG. 3, the tracer material 60 is disposed in a capsule 62 made of any suitable material soluble in the fluid or broken during installation and positioned at the blind end 54 of hole 46 with a plug 64 made of the same material as the pipe wall 40 welded in place in the hole as shown by a cylindrical weld 66 to hold the tracer material in place adjacent end 54. As shown in FIG. 4, the tracer material can be imbedded in plugs 64, as shown at 66, at various heights with the plugs welded in the hole. As shown in FIG. 5, a vessel 68 containing tracer material 70 under pressure can be mounted in communication with a hole with a pressure indicator 72 mounted on the vessel such that pressure in the vessel can be checked by visual inspection. The embodiments of FIGS. 3 and 4 are preferred for radioactive tracer materials while the embodiment of FIG. 5 is designed for chemical tracer materials. The plug 64 of the embodiment of FIG. 3 can have tracer material imbedded therein similar to the plug shown in FIG. 4; and, with the plugs welded in the holes, the structural integrity of the pipe is maintained. Since the pipes are made of ductile material, the holes formed in the pipe walls do not introduce local stress concentrations which would weaken the pipes. The hole diameters are determined by how much tracer material is required to produce a detectable signal. Only very small amounts of radioactive tracer materials are required for detection; and, thus, the diameters of the holes used for radioactive materials are dependent upon the packaging of the radioactive materials and the welding techniques used to position the tracer materials in the holes. When chemical or non-radioactive tracer materials are utilized, the diameters of the holes are determined by the volume necessary to obtain a detectable concentration of the tracer materials in the fluid. If the minimum required concentration of a chemical tracer material for detection in the fluid is $C_{min}$, then the volume of the hole V is given by $$V = \frac{M}{r \times C_{min}}$$

where M is the mass of the fluid in the piping system and r is the density of the tracer material.

It is not necessary to insert tracer materials in every section of a piping system. The determination to be made in implementing the present invention is to designate those sections particularly susceptible or vulnerable to erosion/corrosion, such sections normally including areas of fluid flow turbulence, such as elbows, tees, orifices and pipe bends. These sections or components may be very large and may contain regions varying considerably in erosion/corrosion characteristics. The identification of these sections or regions can be accomplished by the determination of the local mass transfer coefficients as is conventionally calculated in normal engineering practice.

FIGS. 6a–6h disclose piping system components typically subject to turbulence and thinning due to erosion/corrosion, respectively, an elbow, a tee, a junction, a diffuser, an orifice, a corner, a cavity and a flow obstruction. Tracer material inserts are positioned at locations A where the mass transfer coefficient is maximum and locations B determined by the configuration of each particular component. For example, location B for the elbow of FIG. 6a is spaced from location A by a distance equal to 1.5 times the diameter of the pipe. Location B for the tee of FIG. 6b is disposed at a corner with location A aligned with the stem of the tee. Location B for the junction of FIG. 6c is spaced from the point of flow path convergence by a distance equal to 1.5 times the diameter of the lower pipe with location A at the stagnation point. Location A for the diffuser of FIG. 6d is disposed at the point of divergence with location B disposed at the end of divergent pipe. Location A is disposed centrally in the orifice of FIG. 6e with location B spaced downstream by a distance equal to 0.5 times the orifice length. A single location A is disposed in the corner of FIG. 6f. A single location A is disposed centrally in the cavity of FIG. 6g, and location A is disposed immediately upstream of the obstruction of FIG. 6h with location B disposed immediately downstream. By providing holes and tracer materials at both locations A and B, uncertainties inherent in calculations of mass transfer coefficients, commonly in the 10% to 20% range, can be overcome. Additionally, by the use of a plurality of holes bored to varying depths as illustrated in FIG. 2, an accurate indication of the rate of thinning from erosion/corrosion can be determined.

The selection of tracer materials for insertion in the holes is determined by considerations specific to each piping system in particular; however, as a general rule, the tracer materials should not diffuse out of the metal prior to direct exposure to fluid within the piping system, should not react in any way with the metal, should not release radioactive doses to the environment beyond acceptable limits, should not be masked by background noise upon entering the fluid, should not cause corrosion to components in other parts of the piping system following dissolution in the fluid and should not require frequent replacement. Preferably, the tracer materials selected should provide a clear and distinct signal upon entering the fluid to permit distinct identification of each location of pipe thinning, and should readily dissolve in the fluid. The selection of a particular tracer material, whether a chemical, a stable isotope or a gamma or beta emitting isotope, will depend on piping system factors such as instrumentation capabilities, frequency of leaks causing radioactive contamination of the fluid and type of demineralizers utilized. For example, if a piping system is already equipped with an on-line gamma ray detection capability and secondary loop history shows little radioactive contamination, a good tracer material matrix can be represented by Co-60, Eu-154, Li and K. Co-60 is easily detected because of its two distinct energy peaks and has a fairly long half life, and the use of Co-60 with Li as one tracer material in the system will allow distinguishing of other tracer materials formed of Co-60 and K or Co-60 and Li in different concentrations. Thus, the detection of Co-60 and K in the fluid provides a warning that a specific component or section in the piping system is thinning and requires constant monitoring.

To assure that the Co-60 and K entered the fluid from a specific location and not from other sources, the radiation levels at the suspected location can be measured with the reduction in the local radioactivity providing a double check and definite indication of wall thinning. Additionally, if each hole at a location contains a different Co-60 to K ratio, the rate of thinning can be calculated from the time interval between tracer materials from successive holes entering the fluid and the known depths and residual thicknesses of the holes. This information is useful in deciding whether the piping system can be allowed to operate until the next scheduled downtime or should be shut down for immediate repair and provides advanced lead time for ordering replacement pipes. The amounts of Co-60 required are dictated by the background activity in the fluid and occupational standards. In a typical pipe having a diameter of 2 feet with flow velocity of 15 cfs, the introduction of 0.1 micro grams of Co-60 into the fluid produces an activity level of $5 \times 10^{-5}$ $\mu$Ci/cm$^3$ thirty feet downstream which is fifty times higher than the background activity. The radiation exposure one foot away from the pipe can be maintained within the allowable range of 1 mr/hr by placing shielding on the outer surface of the pipe.

If a piping system is not equipped with gamma detectors, it may be desirable to employ beta emitters, such as Ni-63 for example. When beta emitters are used as the tracer material, they are detected from fluid samples which are routinely collected. As the piping system ages, the frequency of analyzing the samples will be increased. With erosion generally being very slow, analysis on a monthly basis should be adequate for a piping system exceeding 70,000 hours of operation.

Stable isotopes can be conveniently used in piping systems equipped with mass spectrometers; and, where the piping system utilizes stable isotopes but no mass spectrometer facility is available on line, fluid samples will be periodically collected for analysis. Where chemical elements or compounds are used as the tracer material, the independent verification afforded by checking radioactivity at a suspected location is not available; however, this can be overcome by the use of the pressure indicator 72 illustrated in FIG. 5 producing a visual indication of the reduction in pressure in the vessel.

The rate at which the tracer materials are released to the fluid within the piping system depends on the specific tracer materials utilized and the method of detection. When the tracer material is in the form of a soluble salt, the tracer materials will be released instantly into the fluid whereas, when the tracer material layers are varied, as illustrated in FIG. 4, a controlled slower rate, as desired, can be obtained.

The following table shows typical tracer materials for use with the present invention:

| Specie | Half Life Years | Rad. Mev (max) | Coolant Bkgd. $\mu$ Ci/gr $\times 10^{-7}$ | Spec. Act. Ci/gr | Min. Mass $\mu$ gr | Reg. Mass $\mu$ gr | Curies $\mu$ Ci | Dose 6 CE mr/hr | MAX. Shield in. |
|---|---|---|---|---|---|---|---|---|---|
| Co-60 | 5.2 | 1.17 | 0.22 | 1130 | 0.0056 | 0.56 | 630 | 4.4 | 1 |
| Cs-137 | 30 | 0.66 | 4.4 | 87 | 1.47 | 147 | 12789 | 50 | 2 |
| Na-22 | 2.6 | 1.28 | 1 | 6250 | 0.004 | 0.4 | 2500 | 19 | 1 |
| Eu-152 | 12 | 1.4 | 1 | 197 | 0.14 | 14 | 2758 | 23 | 2 |
| Mn-34 | 0.83 | 0.833 | 4 | 8000 | 0.013 | 0.13 | 1000 | 5 | 1 |
| Ba-133 | 7.2 | 0.356 | 1 | 374 | 0.07 | 7 | 2618 | 5.6 | 1 |
| Br-90 | 28 | | 0.005 | 141 | 0.001 | 0.1 | 14.1 | | |
| Cd-113 | 13.6 | 0.5 | negl. | | | | | | |
| Br-88 | Stable | | | | | | | | |

The method of the present invention will be explained with respect to a portion of a piping system as illustrated in FIG. 7 for exemplary purposes, the piping system including a straight section of pipe 74 having a wall thickness of 0.6 inches which is dead ended at 76 on one side, receives flow through a pipe 78 adjacent end 76 and has a 90° elbow 80 on an opposite side through which flow exits. Holes and tracer material inserts are disposed at the vena contracta 82, the dead end corner 84, the stagnation point of the tee 86, downstream of a weld 88 at 90 in the straight section of pipe, in both bends of the elbow 80 at 92 and 94, and at the orifice 96 as shown at 98. At location 82, a 0.250 inch hole is drilled to a depth of 0.40 inches and filled to a depth of 0.20 inches with a mixture containing 0.01 gram of CoNO$^3$ salt and 0.1 gram of Li. This mixture can be obtained from isotope suppliers and also contains 0.56 microgram of Co-60. In the remaining 0.20 inches of the hole, an appropriate plug is inserted and welded to the pipe wall as illustrated in FIG. 3. Another hole is drilled at a distance of 0.5 inches from the first hole to a depth of 0.30 inches. To distinguish the second hole from the first hole, the second hole is filled with a mixture containing 0.01 gram of CoNO$^3$, 1.2 microgram Co-60 and 0.01 gram Li. The same procedure is utilized to provide spaced holes at locations 84 and 86. At location 90, more then two holes are drilled to compensate for the uncertainty in determining the points of maximum turbulence and mass transfer in the straight pipe. The first two holes at location 90 are positioned at the downstream corner of the weld pipe interface and, preferably, two additional holes are drilled to a depth of 0.30 inches each at distances of 0.5 and 1.5 times the pipe diameter downstream of the weld such that a total of four holes are drilled at location 90. With respect to elbow 80, at locations 92 and 94 the same procedure as described with respect to location 82 is repeated with the exception that different species are inserted for identification purposes. For example, instead of Co-60, Na-22 is utilized. The holes are filled with a metallic mixture of NaK containing 0.40 micrograms of Na-22. At location 98 in orifice 96, a combination of Ba-133 and Cd-113 could be employed.

After tracer material inserts have been positioned as described above, the piping system is examined for less obvious but equally important local conditions that might give rise to high pipe thinning rates, such as at the joint between two dissimilar materials where one material is more susceptible to erosion than the other creating a flow discontinuity causing high local turbulence and increased erosion. The latter case is illustrated in FIG. 8 wherein material 104 joins material 106 at a junction 108 with material 104 having increased erosion resistance relative to material 106. Using normal erosion rates for materials 104 and 106 and the local flow velocity, the thickness of the boundary layer can be calculated; and, if the resultant increase in local mass transfer coefficient is low, no tracer material need be located at the joint. If, however, the increase is large, a hole 110 is positioned at a distance downstream where a cavity 112 would be formed as determined by normal engineering calculations. This situation exists in many steam generators where the J tubes are made of Inconel and are welded to a feedring made of carbon steel.

Referring again to FIG. 7, a detector 114 is disposed downstream of a flow valve 106 to identify any gamma emitting isotopes entering the fluid passing through the piping system. Such a detector can be a standard gamma ray spectrometer with germanium (Ge/Li) detector with accompanying electronic scales, printing devices and non-proprietary computer programs to process spectral data and calculate radionuclide activities for each isotope. For example, an ABTEC Germanium C515-B-31C detector can be utilized with an ND 680 multi-channel analyzer. Utilizing the detector 114, a specific isotope utilized in the tracer materials can be detected, and the location where pipe wall thinning allowed the isotope to enter the fluid can be determined. The fluid can further be checked by standard and chemical analysis; and, if Li is detected, it can be determined that the tee is the source of the isotope and concomitant pipe wall thinning. For further verification, a standard radiation detector can be placed adjacent the suspected tee location; and, if a reduction in radioactivity at the location is sensed, after correcting for natural decay, a second independent and definitive indication that the warning signal is real will have been obtained. A thinning rate can be determined by dividing the residual wall thickness $R_1$ by the time elapsed between installation of the tracer insert and detection of the tracer material; and, when, after an interval of time, a second warning signal is obtained from the location at the tee, the rate of pipe wall thinning can again be determined by dividing the residual wall thickness differential at the tee, $R_2-R_1$, by the time interval to produce two points of a thinning rate plot and to allow the time remaining for safe operation of the piping system to be determined.

As will be appreciated from the above, the method of the present invention can be employed with existing piping systems as well as with new piping systems. With respect to the former, access is required only to the outside of pipes to be monitored to bore holes and insert tracer materials thus requiring minimum downtime of the piping system. With respect to new piping systems, holes can be bored and filled with tracer materials when the pipes are fabricated with little additional expense.

The term "pipes" as used herein includes all components or parts of piping systems, such as those shown in FIG. 6, as well as heat exchangers, tubs and vessels with or without internal piping, and the term "piping system" as used herein includes systems or networks of pipes for fluid flow. The term "tracer material" as used herein includes relatively stable materials that will not substantially change characteristics over time and can be detected in fluid without dissolving, such as chemical compounds and radioactive isotopes. The rate of release of the tracer materials is preferably fast after rupture of the residual wall thickness associated with a hole; however, a slow release may also be desirable over a longer period of time for some applications. The residual thicknesses are chosen to provide maximum warning time of pipe wall thinning and, as mentioned above, to permit calculation of the rate of thinning. The depths of the holes are related to the thickness of the pipe walls as described above and the diameters of the holes are determined by the volume required for the tracer materials. The holes can be formed or bored in any conventional manner, such as by mechanical, laser or electron beam drilling, and can have any shape, the shape normally determined by boring and welding techniques. To this end, the holes can be conical or widened near the outer surface of the pipe walls. By use of welded plugs to secure tracer materials in the holes, structural integrity of the pipe walls is maintained.

It is understood that temperature, material composition, water chemistry and fluid turbulence affect erosion/corrosion in single phase water flow. In case of steam, the degree of moisture content is an additional important variable. In the past, these parameters have been used to predict locations in a piping system which are susceptible to erosion, and global mass transfer coefficients are used. In other words, average values over an entire component. In accordance with the present invention, local mass transfer coefficients, which are indicative of the local turbulence at points of interest, are used. The local mass transfer coefficients are obtained from available literature. For geometries where such data is not available, a fluid dynamics code, such as COMMIX, available to the public at the Argon National laboratories, is used to determine the local turbulence for complex as well as standard geometries. To account for uncertainties in locating the tracer material inserts, a plurality of tracer material inserts are used. To further reduce uncertainties in locating the tracer material inserts, a plurality of tracer material inserts are used. To further reduce uncertainties in tracer material insert locations, when any indication of unusually high pipe thinning rates occurs, the entire pipe section should be ultrasonically tested. Thus, it will be appreciated that the method of the present invention can be utilized to locate areas of high pipe thinning to permit more comprehensive testing, for example with the use of ultrasonics, without requiring an undue number of tracer material inserts.

Inasmuch as the present invention is subject to many variations, modifications and changes in detail, the above description of the preferred embodiments is meant to be illustrative and not to be taken in a limiting sense.

What I claim is:

1. A method of monitoring wall thickness of pipes in a piping system comprising the steps of:
    boring holes in the outer surfaces of walls of the pipes at predetermined locations along the pipes and to depths larger than the thicknesses at which the pipes will rupture leaving residual wall thicknesses between the ends of the holes and the inner surfaces of the walls;
    inserting tracer materials in the holes to be released into fluid in the piping system when pipe wall thinning exceeds the residual wall thickness at any of the holes;
    monitoring fluid flow through the piping system to sense the presence of the tracer materials in the fluid; and
    determining the location of the hole from which the tracer material was released whereby pipe wall thinning can be detected prior to rupture and thinning of particular pipes within the piping system can be determined to facilitate repair with minimal downtime of the piping system.

2. The method as recited in claim 1 wherein said step of inserting tracer material includes inserting different tracer materials in different holes to associate each tracer material with a predetermined location and said step of determining the location of a hole from which a tracer material was released includes analyzing the sensed tracer material.

3. The method as recited in claim 1 wherein the tracer materials are radioactive and said step of determining the location of the hole from which a sensed tracer material was released includes measuring the radiation external of the piping system to find locations with reduced radioactivity.

4. The method as recited in claim 1 wherein the tracer materials are maintained in the holes under pressure in vessels and pressure indicators communicate with each vessel to produce a visible signal upon reduction in pressure within the vessels and said step of determinig the location of the hole for which the tracer material was released includes visual inspection of the pressure indicators.

5. The method as recited in claim 1 wherein said step of boring holes includes determining the predetermined locations as positions of maximum turbulence with the use of mass transfer coefficients.

6. The method as recited in claim 5 wherein said step of boring holes includes boring two spaced holes at a predetermined location to allow for uncertainties in determining positions of maximum turbulence.

7. The method as recited in claim 6 wherein the two spaced holes have the same depth.

8. The method as recited in claim 1 wherein said step of boring holes includes boring first and second holes at a predetermined location to first and second depths to produce first and second different residual wall thicknesses and further comprising the step of determining the rate of pipe wall thinning at the predetermined location by dividing the difference in residual wall thickness by the time elapsed between sensing tracer materials from the first and second holes.

9. The method as recited in claim 1 wherein said step of inserting tracer materials in the holes includes welding plugs in the holes to seal the tracer materials therein.

10. The method as recited in claim 9 wherein the plugs are made of the same material as the pipes in which they is welded.

11. The method as recited in claim 1 wherein the tracer material is a chemical composition under pressure.

12. A method of monitoring thinning of a pipe carrying a fluid comprising the steps of:
    boring a hole in the outer wall of the pipe to a predetermined depth greater than the wall thickness at which the pipe will rupture to produce a blind end spaced from the internal surface of the pipe wall by a predetermined residual wall thickness,
    inserting a tracer material in the hole adjacent the blind end, and
    monitoring the fluid passing through the pipe to sense presence of the tracer material whereby pipe thinning corresponding to the residual wall thickness can be detected.

13. The method as recited in claim 12 and further comprising the step of welding a plug made of the same material as the pipe in the hole to seal the tracer material therein.

14. The method as recited in claim 13 wherein the tracer material is radioactive.

15. The method as recited in claim 12 wherein a second hole is bored adjacent the first hole to a predetermined depth less than the predetermined depth of the first hole to produce a predetermined residual wall thickness greater than the predetermined residual wall thickness of the first hole, a tracer material is inserted in the second hole, the fluid is monitored to sense presence of tracer materials from the first and second holes and the rate of thinning of the pipe wall is determined from the time between sensing of the tracer materials and the difference in the residual wall thicknesses of the first and second holes.

16. The method as recited as claim 12 and further comprising the step of determining the rate of pipe wall thinning from the time when the tracer material is sensed and the residual wall thickness.

* * * * *